US00PP24742P3

(12) United States Plant Patent
Bédard

(10) Patent No.: US PP24,742 P3
(45) Date of Patent: Aug. 12, 2014

(54) MINIATURE ROSE PLANT NAMED 'WEKTEBODOKO'

(50) Latin Name: *Rosa hybrida*
Varietal Denomination: WEKtebodoko

(71) Applicant: Early Morning LLC, Pomona, CA (US)

(72) Inventor: Christian Bédard, Brea, CA (US)

(73) Assignee: Early Morning LLC, Pomona, CA (US)

( * ) Notice: Subject to any disclaimer, the term of this patent is extended or adjusted under 35 U.S.C. 154(b) by 64 days.

(21) Appl. No.: 13/694,365

(22) Filed: Nov. 26, 2012

(65) Prior Publication Data

US 2014/0150140 P1 May 29, 2014

(51) Int. Cl.
*A01H 5/00* (2006.01)

(52) U.S. Cl.
USPC ..... Plt./116

(58) Field of Classification Search
CPC ..... A01H 5/0222; A01H 5/0216; A01H 5/02; A01H 5/00
USPC ..... Plt./116
See application file for complete search history.

(56) References Cited

U.S. PATENT DOCUMENTS

PP16,202 P2 1/2006 Radler

*Primary Examiner* — Kent L Bell
(74) *Attorney, Agent, or Firm* — McKee, Voorhees & Sease, P.L.C.

(57) ABSTRACT

A new variety of Miniature rose suitable for garden decoration, having flowers of painted pink & white coloration.

1 Drawing Sheet

Classification: The present invention relates to a new *Rosa hybrida* plant.

Variety denomination: The new plant has the varietal denomination 'WEKtebodoko'.

BACKGROUND OF THE INVENTION

This invention relates to a new and distinct variety of Miniature Rose. It has as its seed parent the variety known as 'WEKiscorou' (not patented) and as its pollen parent the variety known as 'RADtko' (U.S. Plant Pat. No. 16,202).

SUMMARY OF THE INVENTION

Among the features which distinguish the new variety from other presently available and commercial rose cultivars known to the inventor are the following combinations of characteristics: its unusual painted pink & white flower coloration, its excellent color stability throughout the life of the flower and its large flower size for the class. The plant has a bushy rounded moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKtebodoko' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKiscorou' by the following combination of characteristics: whereas 'WEKtebodoko' bears flowers of painted pink & white coloration, 'WEKiscorou' bears flowers of scarlet and white bicolor coloration. The new variety is classified as a Miniature rose with a bushy rounded moderately spreading somewhat tall growing habit (about 92 to about 120 cm. in height), whereas the seed parent is classified as a Shrub rose with a bushy compact significantly shorter growing habit (about 62 to about 75 cm. in height).

The new variety may be distinguished from its pollen parent, 'RADtko' by the following combination of characteristics: whereas 'WEKtebodoko' bears medium flowers (about 4.8 to about 6.5 cm. in diameter) of painted pink & white coloration, 'RADtko' bears significantly larger flowers (about 8.0 cm. in diameter) of red coloration. The new variety is classified as a Miniature rose with a bushy rounded moderately spreading growing habit (about 108 to about 158 cm. spread at the widest point), whereas the pollen parent is classified as a Shrub rose with a round and bushy significantly more compact growing habit (about 100 cm. spread at the widest point).

COMPARISON WITH THE CLOSEST COMMERCIALLY AVAILABLE CULTIVAR

The new variety may be distinguished from its closest commercially available cultivar, 'WEKsybil' (U.S. Plant Pat. No. 7,588) by the following combination of characteristics: whereas 'WEKtebodoko' bears double flowers (about 18 to 25 petals) of painted pink & white coloration, 'WEKsybil' bears double flowers of deep pink to red with a white eyezone and reverse coloration with heavier petalage (about 24 to 28 petals). The new variety has a bushy rounded moderately spreading somewhat tall growing habit (about 92 to about 120 cm. in height), whereas the closest commercially available cultivar has a dwarf, bushy, upright significantly shorter growing habit (about 46 to about 62 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong somewhat short stems (about 11 to about 26 cm.). Outdoors, the plant blooms abundantly and nearly continuously during the growing season. The flowers have a slight fruity to apple-like fragrance.

BUD

The peduncle is about 1.9 to about 5.1 cm. in length, of average caliper (about 0.2 to about 0.3 cm. in diameter), and usually erect. It is moderately rough, with some stipitate glands. Peduncle color is between 144A and 146B often moderately suffused, especially on the side exposed to the sun, with between 183A and 187A.

Before the calyx breaks, the bud is about 0.7 to about 1.3 cm. in diameter at the widest point, about 1.2 to about 1.8 cm. in length, and pointed to somewhat ovoid in shape. The surface of the bud bears between 8 to 11 foliaceous appendages and very few stipitate glands, usually with slender entire foliaceous parts extending beyond the tip of the bud about ½ or more of its length. Bud color is between 146B and 146A often moderately suffused, especially on the side exposed to the sun, with between 183A and 187A.

The sepals are about 1.9 to about 2.8 cm. in length and about 0.6 to about 0.9 cm. in width at the widest point. The outer surface color of the sepal is between 146B and 146A often moderately suffused, especially on the side exposed to the sun, with between 183A and 187A. The outer surface of the sepal is smooth and bears between 2 to 4 foliaceous appendages with very few stipitate glands. After the sepals open, the inner surface color is sometimes heavily suffused, especially on the area exposed to the sun, with between 187A and 187B. The inner surface color of the sepal is near 146B broadly bordered by near 139A. The inner surface of the sepal is covered with fine wooly tomentum; sepal margins are lined with some stipitate glands and hairs.

The receptacle of the flower is of medium to somewhat long length (about 0.5 to about 0.6 cm.) and moderately heavy in caliper (about 0.4 to about 0.7 cm. in diameter). The receptacle is urn-shaped in form. Its surface is smooth with thick fleshy walls. The receptacle color is between 144A and 146B.

As the petals open (after the calyx breaks), the bud is about 1.2 to about 1.6 cm. in diameter at the widest point, about 1.9 to about 2.5 cm. in length, and moderately ovoid to somewhat pointed in form. The color of the under surfaces of the newly opened petals is between 3C and 4B sometimes lightly suffused with between 59C and 60C. There is no visible change in coloration at the point where the petal attaches. The color of the upper surfaces of the newly opened petals is between 3C and 4B usually heavily overlaid on the upper half of the petal with an irregular wash of between 54A and 54B. There is no visible change in coloration at the point where the petal attaches.

BLOOM

When fully open, the bloom ranges from about 4.8 to about 6.5 cm. in diameter. Petalage is double with about 18 to 25 petals and about 1 to 3 petaloids irregularly arranged. When partially open, the bloom form is somewhat ovoid to moderately cupped, and the petals are loosely spiraled to cupped with petal edges somewhat reflexed outward. When fully open, the bloom form is more cupped, and the petals are loosely cupped with petal edges moderately reflexed outward.

PETALS

The substance of the petals is moderately heavy and of medium to somewhat thick thickness, with upper surfaces moderately satiny and under surfaces slightly shiny to matte. The petals are about 2.1 to about 3.6 cm. in length and about 1.3 to about 3.2 cm. in width at the widest point. Petal margins are entire.

The outer petals are nearly obovate in shape with rounded apices to sometimes slightly mucronate.

The inner petals are somewhat obovate to moderately oblanceolate in shape with rounded apices to sometimes slightly mucronate.

Petaloids are about 1.2 to about 2.5 cm. in length and about 0.5 to about 1.3 cm. in width at the widest point. Petaloids are irregularly shaped somewhat oblanceolate to subulate with rounded apices.

NEWLY OPENED FLOWER

The under surface color of the outer, intermediate and inner petals is between 2D and 36D sometimes lightly suffused with near 60D. There is no visible change in coloration at the point where the petal attaches. The upper surface color of the outer, intermediate and inner petals is between 2D and 11D usually heavily overlaid on the upper half of the petal with an irregular wash of between 61C and 57C. At the point where the petal attaches, there is a small zone of between 3C and 4B.

The under and upper surface colors of the petaloids are similar in coloration to the upper and under surfaces of the intermediate and inner petals.

The general tonality of the newly opened flower is between 2D and 11D usually heavily overlaid on the upper half of the petal with an irregular wash of between 61C and 57C.

THREE-DAY-OLD FLOWER

The under surface color of the outer, intermediate and inner petals is between 2D and 36D sometimes lightly suffused with near 60D. There is no visible change in coloration at the point where the petal attaches. The upper surface color of the outer, intermediate and inner petals is between 2D and 11D usually heavily overlaid on the upper half of the petal with an irregular wash of between 61C and 57C. At the point where the petal attaches, there is a small zone of near 3C.

The under and upper surface colors of the petaloids are similar in coloration to the upper and under surfaces of the intermediate and inner petals.

The general tonality of the three-day-old flower is between 2D and 11D usually heavily overlaid on the upper half of the petal with an irregular wash of between 61C and 57C.

On the spent bloom, the petals usually drop off cleanly and are not particularly affected by cold, hot, wet, or dry weather.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 105) and are arranged regularly about the pistils; a few are mixed with petaloids. The filaments are of somewhat long length (about 0.4 to about 1.0 cm.) most with anthers. Filaments are between 3B and 5B in color. The anthers are of medium size for the class and all open approximately at the same time. Anther color when immature is near 22A on the external part and near 13D on the internal part. Anther color at maturity is near 164C on the external part and near 200A on the internal part. Pollen is moderately abundant and between 19C and 18B in color.

FEMALE REPRODUCTIVE ORGANS

Pistils vary in number (average about 55). The styles are moderately uneven, somewhat long in length (about 0.4 to about 0.7 cm.), thin in caliper, and loosely bunched. Stigma color is near 13B. Style color is between 150B and 150C sometimes lightly suffused with between 53C and 53D. Ovaries are usually all enclosed in the calyx.

Hips are of moderately short length (about 1.1 to about 1.5 cm.), rounded in form, and between 31A and 32A in color when ripe. The hip surface is smooth with thick fleshy walls. The sepals are moderately permanent, and usually straight in shape.

The seeds are irregularly rounded, smooth in texture, approximately 3 to about 9 per hip, about 0.3 to about 0.6 cm. in diameter at the widest point and between 164D and 165D in color.

FOLIAGE

The compound leaves are usually comprised of three to seven leaflets and are borne abundantly. The five-leaflet leaves are about 5.2 to about 9.2 cm. in length and about 3.7 to about 6.4 cm. in width at the widest point, leathery to somewhat crisp in texture, and glossy in finish on the upper side and slightly shiny in finish on the under side. The leaves have a pinnate venation pattern. The terminal leaflets are about 2.0 to about 3.7 cm. in length and about 1.2 to about 2.2 cm. in width at the widest point, shaped ovate to somewhat oval with acute apices and rounded to somewhat acute bases. Their margins are usually simply serrate.

The upper surface color of the mature leaf is between 139A and 147A. The under surface color of the mature leaf is between 147B and 148A. The under and upper colors of the leaf veins on the mature leaf are similar in coloration to the upper and under surfaces colors of the mature leaf. The upper surface color of the young leaf is between 137B and 146A, often heavily suffused with between 187A and 187B. The under surface color of the young leaf is between 146B and 146C, often heavily suffused with between 187B and 187A. The under and upper colors of the leaf veins on the young leaf are similar in coloration to the upper and under surfaces colors of the young leaf.

The rachis is somewhat light to average in caliper and moderately rough. The upper side is deeply grooved with few hairs and some stipitate glands on the edges of the grooves. The under side of the rachis is moderately rough with few stipitate glands and very few small prickles. The rachis color is near 146D on the under side and near 137C on the upper side often heavily suffused on the young leaf with between 183A and 187B.

The stipules are about 0.9 to about 1.4 cm. in length and moderately wide (about 0.4 to about 0.6 cm.) with somewhat long straight points that usually turn out at an angle of more than 45 degrees and sometimes recurve toward the stem. The under and upper surface color of the stipule is between 137A and 137B often heavily suffused, especially on the young leaf, with between 187C and 187B.

The petiole is somewhat light to average in caliper and moderately rough. The upper side is deeply grooved with few hairs and some stipitate glands on the edges of the grooves. The under side of the petiole is moderately rough with few stipitate glands and very few small prickles. The petiole is about 0.2 to about 0.9 cm. in length and about 0.1 to about 0.15 cm in width at the widest point. The petiole color is near 146D on the under side and near 137C on the upper side often heavily suffused on the young leaf with between 183A and 187B.

The plant displays an above average degree of resistance to powdery mildew and rust as compared to other commercial varieties grown under comparable conditions in Pomona, Calif. known to the Inventor. The plant's winter hardiness and drought/heat tolerance are yet to be determined.

GROWTH

The plant has a bushy rounded moderately spreading somewhat tall growing habit (about 92 to about 120 cm. in height and about 108 to about 158 cm. spread at the widest point), with very full branching. It displays vigorous growth and the canes are of moderately heavy caliper for the class (about 1.8 to about 2.5 cm. in diameter at the widest point).

The color of the major stems is between 146B and 146A. They bear some large prickles that are about 0.8 to about 1.3 cm. in length. The large prickles are almost straight to angle slightly downward with a somewhat short moderately broad oval base; prickle color is near 165A. The major stem bears very few small prickles of similar shape and coloration.

The color of the branches is between 146B and 146A. They bear some large prickles which are of similar shape to the large prickles on the major stems. The prickles are about 0.6 to about 0.8 cm. in length. The prickle color is between 146C and 147C often moderately suffused with between 187C and 187D. The branches bear very few small prickles of similar shape and coloration.

The color of the new shoots is between 146B and 146A often heavily suffused with between 187B and 187A. They bear some large prickles which are of similar size and shape to the large prickles on the branches; prickle color is between 146C and 147C often heavily suffused with between 187B and 187C. The shoots bear very few small prickles of similar shape and coloration.

I claim:

1. A new and distinct Miniature rose plant of the variety substantially as described and illustrated herein.

* * * * *

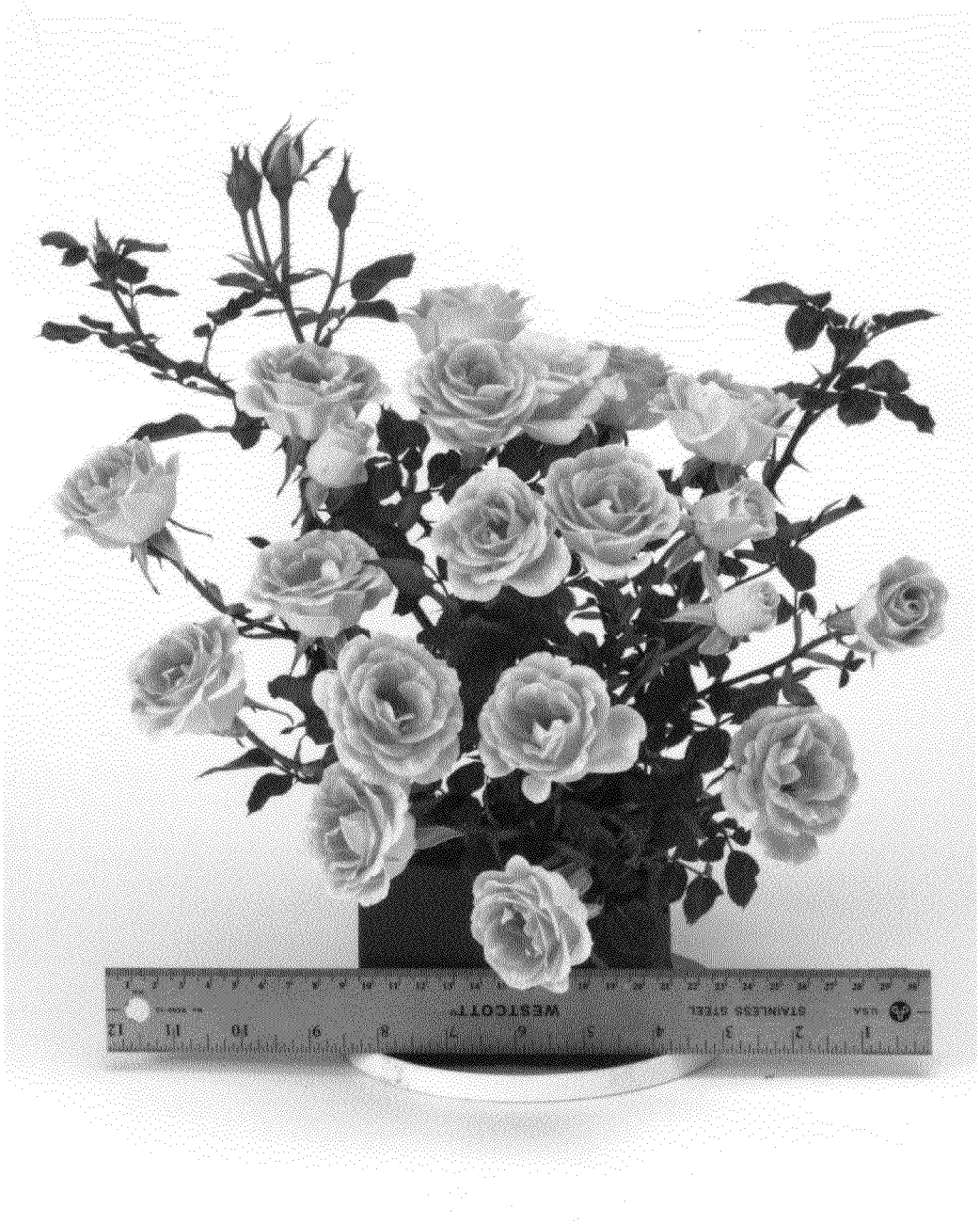
WESTCOTT
STAINLESS STEEL
USA